(12) United States Patent
Alvarez et al.

(10) Patent No.: US 7,318,831 B2
(45) Date of Patent: Jan. 15, 2008

(54) SYSTEM AND METHOD FOR PERFORMING IRRIGATED NOSE AND THROAT SURGERY

(75) Inventors: Edgardo L. Alvarez, Portage, MI (US); Reuben Setliff, III, Sioux Falls, SD (US)

(73) Assignee: Stryker Corporation, Kalamazoo, MI (US)

( * ) Notice: Subject to any disclaimer, the term of this patent is extended or adjusted under 35 U.S.C. 154(b) by 925 days.

(21) Appl. No.: 10/616,654

(22) Filed: Jul. 10, 2003

(65) Prior Publication Data
US 2004/0059363 A1 Mar. 25, 2004

Related U.S. Application Data

(60) Provisional application No. 60/395,881, filed on Jul. 13, 2002.

(51) Int. Cl.
A61B 17/14 (2006.01)
A61F 5/04 (2006.01)

(52) U.S. Cl. ...................... 606/180; 606/170
(58) Field of Classification Search ........ 606/167–180, 606/76–87; 604/22; 128/898
See application file for complete search history.

(56) References Cited

U.S. PATENT DOCUMENTS

| 5,730,752 | A | * | 3/1998 | Alden et al. ............... 606/180 |
| 5,916,231 | A | | 6/1999 | Bays |
| 6,017,354 | A | * | 1/2000 | Culp et al. ............... 606/170 |
| 6,152,941 | A | | 11/2000 | Himes et al. |
| 6,217,543 | B1 | * | 4/2001 | Anis et al. ............... 604/22 |
| 6,221,088 | B1 | | 4/2001 | Bays |
| 6,332,891 | B1 | | 12/2001 | Himes |
| 6,342,061 | B1 | | 1/2002 | Kauker et al. |

OTHER PUBLICATIONS

PCT App. No. PCT/US03/21657 International Search Report, Oct. 2003.
U.S. Appl. No. 09/302,148, filed Apr. 29, 1999.
U.S. Appl. No. 10/251,646, filed Sep. 21, 2002.

* cited by examiner

Primary Examiner—Vy Q. Bui
(74) Attorney, Agent, or Firm—Flynn, Thiel, Boutell & Tanis, P.C.

(57) ABSTRACT

A system and method for performing skull based nasal, sinus and/or throat surgery. In the system and method of this invention a cutting accessory is applied to the tissue on which a procedure is to be performed. Simultaneously with the performance of the procedure by the cutting accessory, irrigating solution is discharged from the cutting accessory onto the tissue. The cutting accessory also has a conduit through which the discharged irrigating solution is drawn away from the surgical site. The irrigating solution discharged onto the surgical site facilitates the performance of the surgical procedure. This solution can also be used to remove debris from the distal end of an endoscope employed to view the procedure and/or as a transport media for topically applying medicine to the surgical site.

18 Claims, 10 Drawing Sheets

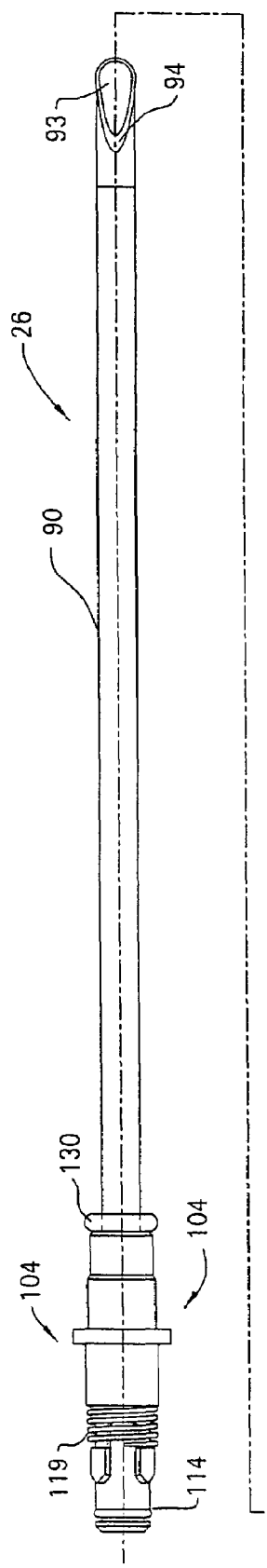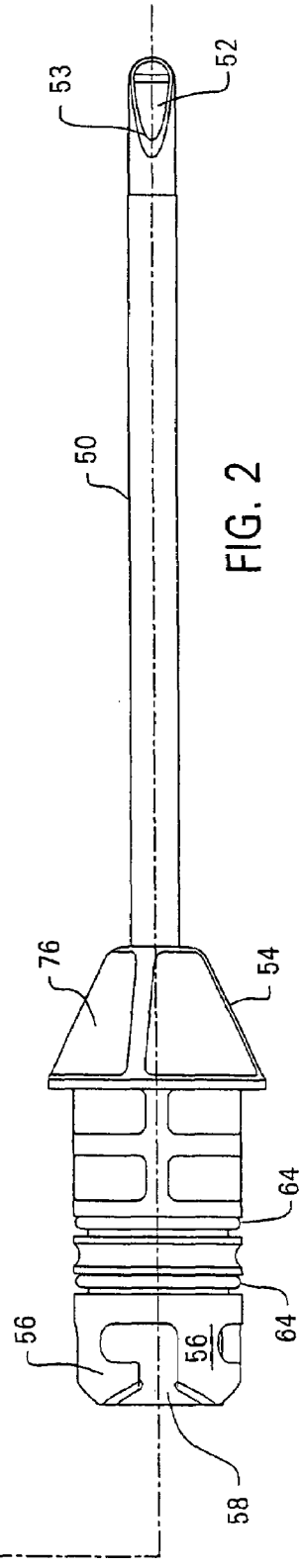
FIG. 2
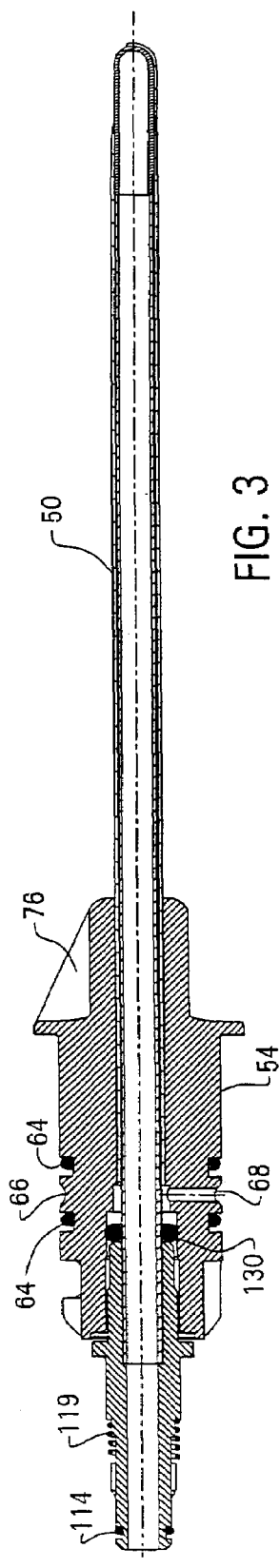
FIG. 3

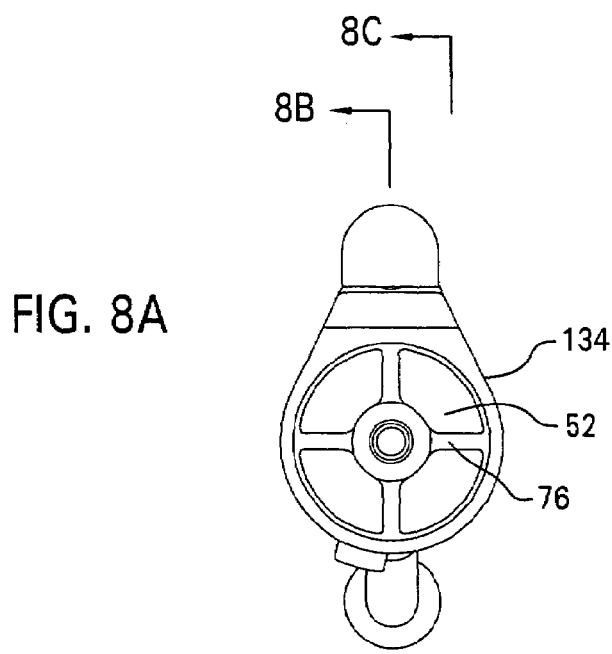
FIG. 8A
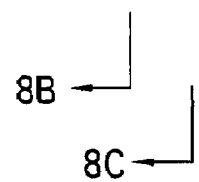
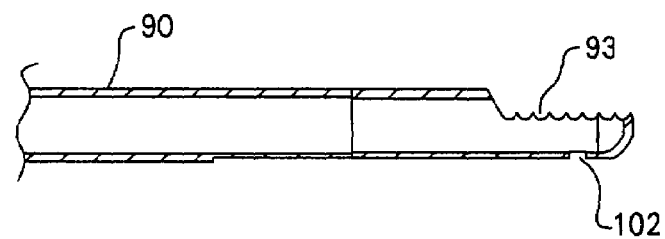
FIG. 5
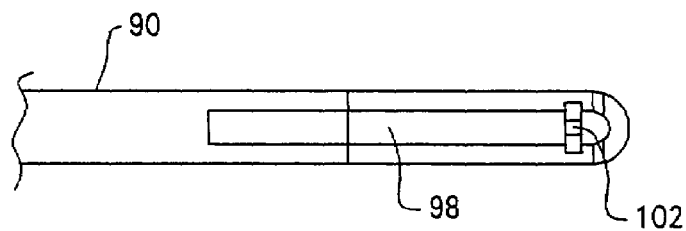
FIG. 6

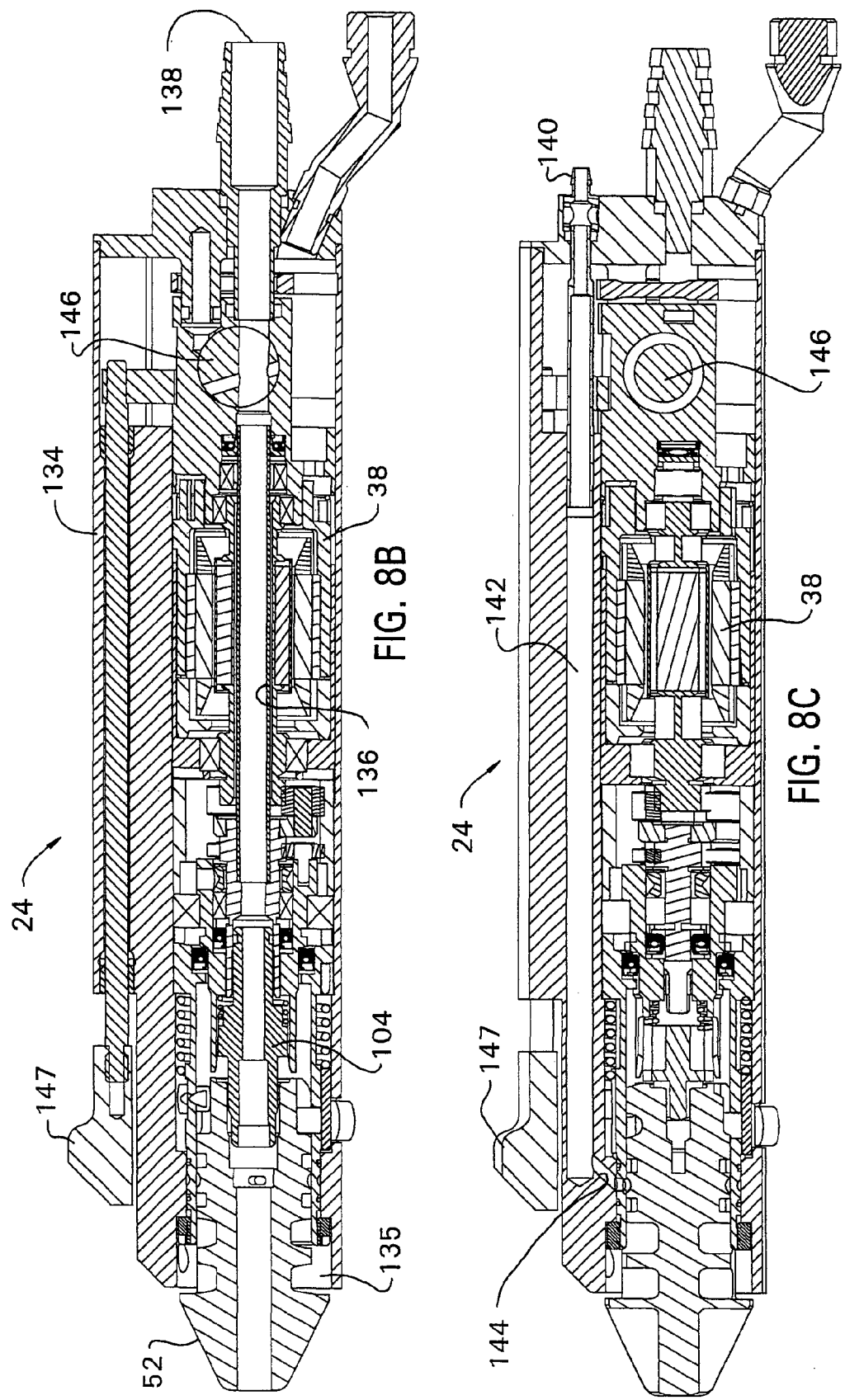

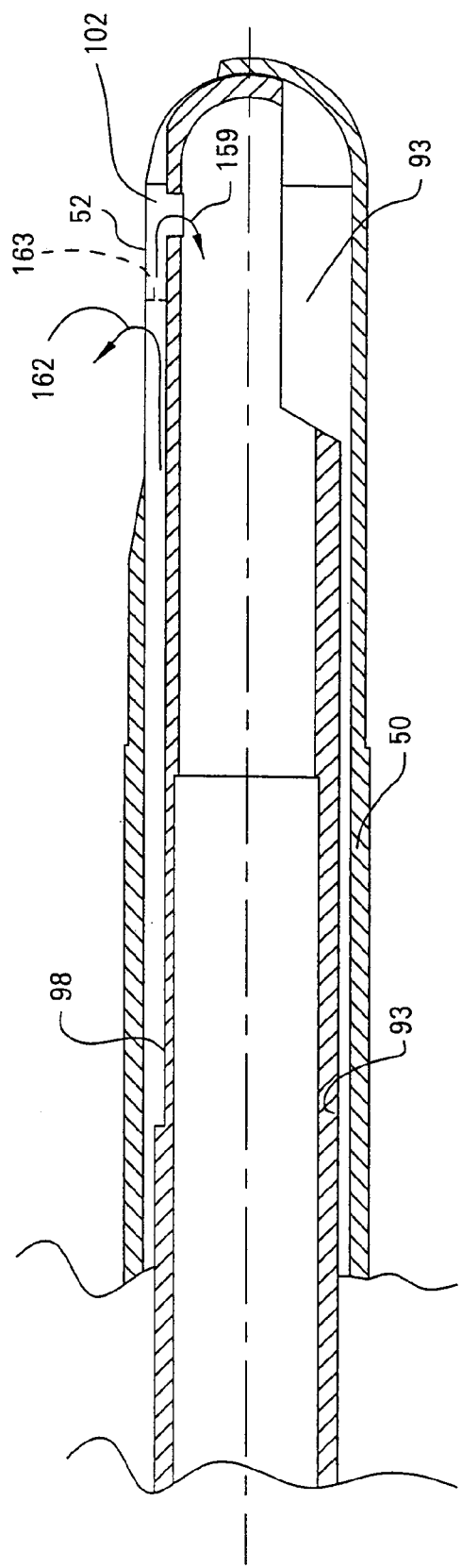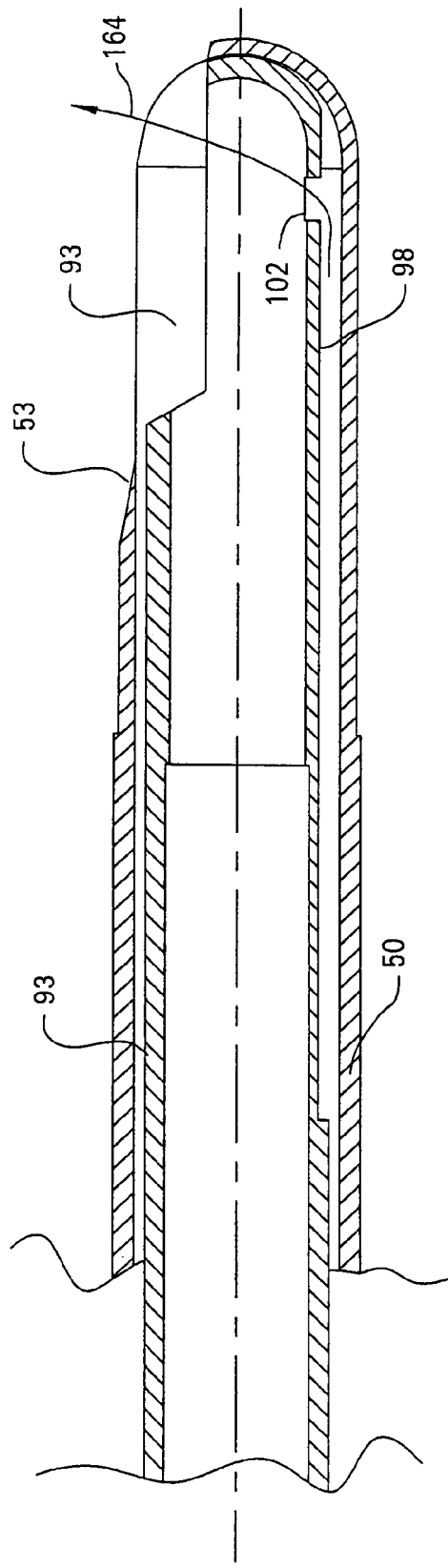

SYSTEM AND METHOD FOR PERFORMING IRRIGATED NOSE AND THROAT SURGERY

RELATIONSHIP TO EARLIER FILED APPLICATION

This application claims priority under 35 U.S.C. Sec. 119 from U.S. Provisional Patent Application No. 60/395,881 filed Jul. 13, 2002.

FIELD OF THE INVENTION

This application relates generally to a surgical system and method designed to perform skull based surgery on tissue within the nose, sinus, throat larynx or trachea. More particularly, this application relates to a system designed to perform surgery on these tissues so as to irrigate the surgical site during the surgical procedure.

BACKGROUND OF THE INVENTION

The goal of many surgical procedures is to remove, and/or remove so as to shape, body tissue at the site at which the procedure is performed. Surgery on the nasal and sinus cavities and/or the throat frequently involves performing this type of selective removal of tissue. For example, sinus surgery often involves the removal of diseased membranes and/or bone partitions and/or malformed portions of the sinus tissue, sometimes referred to as the sinus layer, and any boney material entrained in this layer. It is also often necessary to remove and/or selectively shape both hard and soft tissue that is part of the nasal system for both rhinoplasty procedures and for aesthetic procedures.

A number of instruments and surgical techniques have been developed to facilitate the performance of these surgical procedures. For example, the Applicant's Assignee manufactures a line of surgical tools under the trademark HUMMER that are especially designed to perform nasal, sinus and throat surgery. This line of tools includes a handpiece with an electrically driven motor. Different cutting accessories are designed to selectively fit the handpiece. Each cutting accessory typically has a hollow rotating or reciprocating shaft that is housed in a fixed tube-like outer housing. Irrigating solution is flowed to the distal end of the cutting accessory, the end applied to the surgical site, through an annular space between the moving shaft and the complementary outer housing. Substantially all, if not all, of this fluid is then drawn away from the distal end of the outer housing before it can be discharged from the cutting accessory by a suction that is applied through the rotating or reciprocating shaft. This fluid thus serves as transport media that flushes debris proximally, away from the patient.

Unfortunately, there are some disadvantages associated with the known methods of performing surgery on nasal, sinus or throat tissue. One of these disadvantages is associated with the fact that it is sometimes difficult to cleanly sever the tissue being worked on from the surgical site. This may be due, in part, to the fact that the suction force applied to the surgical site draws the tissue into the cutting accessory. Moreover, the tissue edges are prone to being pinched by the cutting accessory. This pinching can result in even the most skilled surgeon removing more tissue from the surgical site than is necessary to accomplish the desired result. This excess tissue removal can cause unwanted results. For example, during sinus surgery, this pinching can result in large sections of the sinus lining, not just the targeted section, being removed from the surgical site. This can result in unnecessary exposure of bone. Once the tissue lining is removed, the body then generates a new lining. The body's having to generate this new tissue can both delay the complete healing and increase the healing burden on the patient. Further, this new tissue is not as efficient as the lining it replaces.

Another difficulty with known (ear, nose and throat) surgical techniques is associated with the endoscopes that are often used to perform the surgical procedures. An endoscope is an elongated tube that is directed to the surgical site that is capable of transmitting light to and from the site. When the surgical site is at a difficult to reach or view location inside the patient, the surgeon will use the endoscope in order to view the site. An advantage of performing a surgery endoscopically is that it limits the extent to which the patient's body has to be open to the environment in order to gain access to the surgical site. This minimal opening of the patient's body both lessens the extent to which the body is open to infection during surgery and the extent to which it must heal after surgery.

Problems can arise when ENT surgery is performed endoscopically because, as a consequence of performing a surgical procedure, opaque solids and liquids present at the surgical site adhere to the distal end of the endoscope. This material obstructs the view of the surgical site. Presently, there are two ways to remove this material. One can remove the endoscope from the surgical site and wipe off the material that caused the obstruction. This involves withdrawing the endoscope, wiping off the obstructing material and then repositioning it at the surgical site. Moreover, as part of this process, an anti-fogging material applied to the endoscope is removed with the obstruction. This material then needs to be reapplied. Requiring each of these steps to be performed each time the endoscope becomes obstructed adds to the overall time it takes to perform a surgical procedure. This runs contrary to a goal of modern surgery to perform the procedure as quickly as possible in order to keep the time the patient is held under anesthesia as short as possible.

The second means of removing an obstruction is to provide some sort of fluid-dispersing device at the surgical site. Sometimes this device is a stand alone unit. Providing this device requires one to position this device in the vicinity of the surgical site. The presence of this device therefore adds to the number of devices that are positioned at the surgical site. Alternatively, the fluid delivery device is a sheath in which the endoscope is seated. Space between the inner wall of the sheath and the endoscope functions as a conduit through which fluid is delivered. A disadvantage of this arrangement is that it causes the overall diameter of the inserted, distal end portion of the endoscope to appreciably increase. The increase in size of this assembly results in a like increase in the difficulty of inserting the endoscope in position and maneuvering the endoscope.

One technique that has been tried to minimize the above problems associated with ENT surgery, including sinus surgery, is to flood the site at which the procedure is performed with irrigating solution. When other surgical procedures are performed, for example, endoscopic orthopedic surgery, sometimes referred to as arthroscopic surgery, this pool of fluid helps keep debris from adhering to the distal end of the endoscope.

However, when one performs arthroscopic surgery, the fluid is introduced into a substantially closed capsule in a limb. The nose, sinus and throat are different. The passages integral with these organs lead to the lungs. Thus, the flooding of these organs can lead to fluid flowing to other organs that are not intended to receive massive amounts of liquid, especially when a patient is under anesthesia.

Thus, when one tries to flood the nasal cavities, sinuses or throat prior to the actual performance of the surgical procedure, care must be taken to ensure that the solution does not flow to organs in which, if it were allowed to collect, it could potentially harm the patient. Consequently, given the extra steps and care that must be taken when one attempts to immerse a nasal passage or the throat in an irrigating solution in order to perform surgery on the adjacent tissue, it has not proven an especially popular surgical practice in ENT surgery.

SUMMARY OF THE INVENTION

This invention is directed to a new and useful system and method for performing ENT surgery such as surgery on sinus tissue. In the system and method of this invention, a surgical instrument is employed that is designed to discharge an irrigating solution in a specific spray pattern away from the opening in the instrument through which the fluid is discharged. Thus, in the system and method of this invention, the irrigating solution is available to perform more functions than simply serve as transport media for the waste material and fluids drawn through the surgical instrument. Specifically, the spray can be directed towards the distal end of the endoscope in order to remove material that has adhered to the endoscope and that is interfering with the view through the endoscope. The spray is also available to wet the surgical site so as to facilitate the removal of material from the site. Furthermore, the system can also be configured to spray medicine or other fluids beneficial to the surgical procedure directly on the surgical site or an adjacent location.

BRIEF DESCRIPTION OF THE DRAWINGS

The invention is pointed out with particularity in the claims. The above and further features and benefits of the invention may be better understood by reference to the following description in combination with the accompanying drawings, in which:

FIG. 2 depicts the basic components of a cutting accessory of the surgical system of this invention;

FIG. 3 is a cross-sectional view of the cutting accessory of FIG. 2;

FIG. 5 is a cross-sectional view of the distal end of the rotating shaft of the cutting accessory;

FIG. 6 is a back view of the distal end of the rotating shaft of the cutting accessory of this invention;

FIG. 8A is a view, looking proximally, of the front face of a surgical handpiece of this invention;

FIG. 8B is a cross-sectional view of the handpiece of FIG. 8A taken along line 8B-8B;

FIG. 8C is a cross-sectional view of the handpiece of FIG. 8B taken along line 8C-8C;

FIG. 13 depicts one means by which a parcel of water is discharged from the distal end of the cutting accessory;

FIG. 14 depicts a second means by which a parcel of water is discharged from the distal end of the cutting accessory.

DETAILED DESCRIPTION

Figure 1:
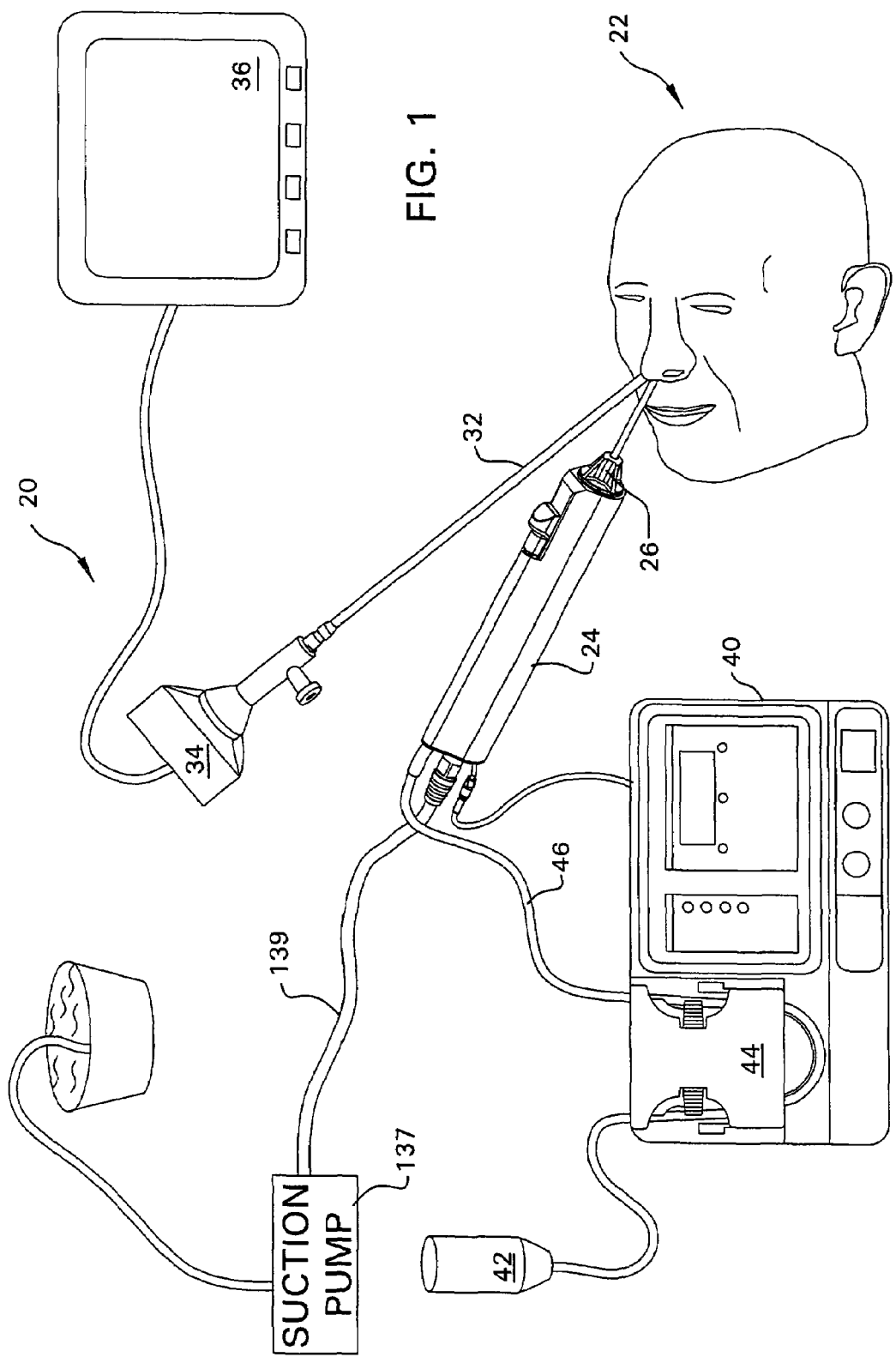
FIG. 1 is an overall view of the components of the surgical system of this invention.

FIG. 1 illustrates how a surgical system 20 of this invention is employed to perform sinus surgery on the head 22 of a patient. System 20 includes a powered surgical handpiece 24 that drives a cutting accessory 26. The cutting accessory is inserted into the nostril or throat 28 of the patient and is positioned against tissue 30 (FIG. 9), at a surgical site where a procedure is to be performed. The surgeon views the surgical site through an endoscope 32. The endoscope 32, which is an elongated device, is inserted through the nostril and positioned so that its distal end is a slight distance proximally away from the surgical site. ("Proximally" shall be understood to mean towards the surgeon/away from the surgical site. "Distally" shall be understood to mean away from the surgeon/towards the surgical site.) Internal to the endoscope are media that transmit the light rays of the image present at the surgical site to the proximal end of the endoscope. These light rays are captured by a camera head 34 attached to the proximal end of the endoscope 32. Video signals generated by the camera head 34 are used to present a view of the surgical site on a monitor 36.

A motor 38 (FIG. 8B) is disposed inside the handpiece 24 for actuating the cutting accessory. Power to energize the handpiece motor 38 is supplied by a control console 40. Control console 40 also supplies irrigating solution from a supply container 42 to the cutting accessory 26. Specifically, control console 40 is provided with a pump 44 that forces fluid that is gravity fed from container 42 through a supply tube 46 that is connected to the cutting accessory 26. In some versions of the invention, the supply tube 46 is connected to a conduit internal to the handpiece 24.

Figure 4A:
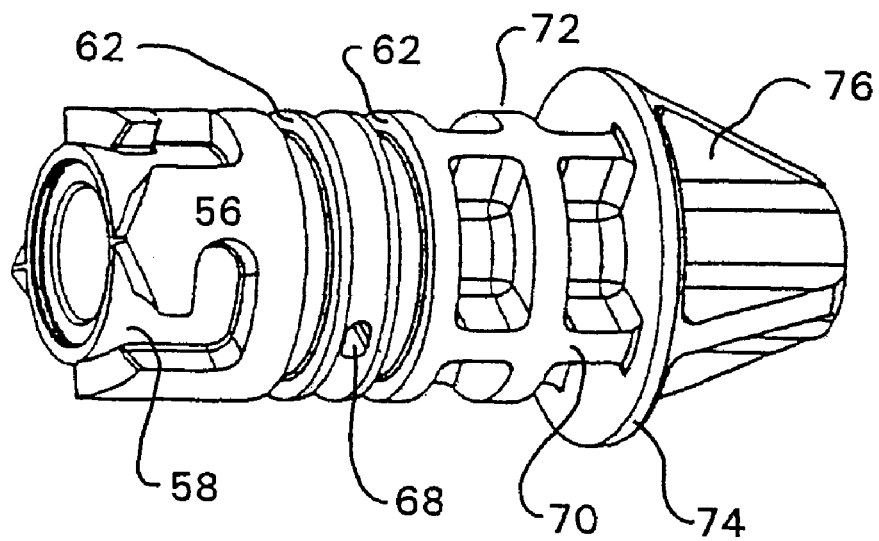
FIGS. 4A and 4B are, respectively, perspective and cross-sectional views of the outer hub of the cutting accessory of this invention.
Figure 4B:
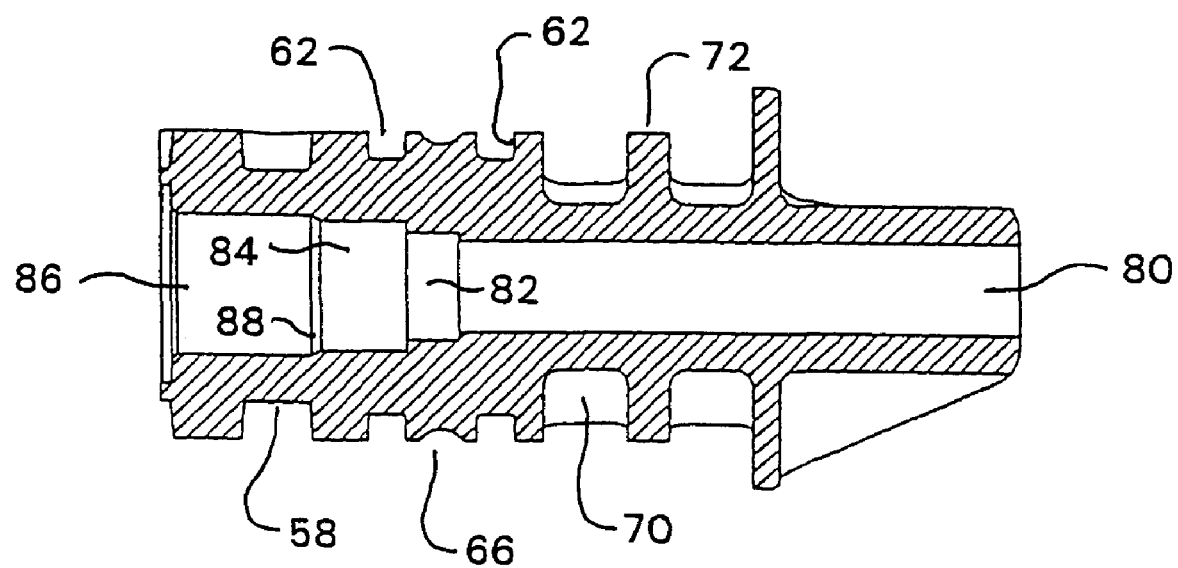

FIGS. 2 and 3 depict the basic components of one cutting accessory 26 that can be used with this invention. Cutting accessory 26 includes a tubularly shaped outer housing 50. The particular cutting accessory, a shaver, is constructed so that the distal end of outer housing 50 is closed. A small window 52 is formed in outer housing 50 proximally to the closed distal end tip of the housing. An outer hub 54, seen best in FIGS. 4A and 4B, is secured to the proximal end of the outer housing 50. Outer hub 54 is a generally tubular member that extends a short distance rearwardly beyond the proximal end of outer housing 50. The outer hub 54 is formed to have a set of spaced apart, generally L-shaped teeth 56. Teeth 56 are shaped to define lock slots 58 between the teeth. When the cutting accessory 26 is seated in the open distal end of handpiece 24, locking members integral with a coupling assembly internal to the handpiece are seated in the lock slots 58. Owing to the geometry of the teeth and lock slots 56 and 58, respectively, the seating of the locking members in the slots holds the outer hub 54, and therefore the rest of the cutting accessory 26, to the handpiece 24.

Extending distally from teeth 56, the outer hub is shaped so as to have two spaced apart, circumferentially extending grooves 62 in the outer surface of the hub. Grooves 62 are shaped to accommodate O-rings 64. The outer hub 54 is further shaped so as to have a relatively shallow concave groove 66 in the outer surface between grooves 62. A bore 68 extends through the outer hub from the base of groove 66 to the underlying axially extending bore in the center of the hub.

Extending distally from the portion of the outer hub 54 that defines the most distal groove 62, the hub is formed to have a set of longitudinally extending spaced apart webs 70. An outwardly directed circumferentially extending flange 72 intersects webs 70. Webs 70 abut and terminate at the proximally directed face of a flat ring 74 that extends around the outside of the outer hub 50. Webs 76, which are aligned with webs 70, extend forward from the distally directed face of ring 74 to the distal end of the outer hub 54. Webs 76 have a triangular profile such that they are at their widest distance from the center axis of hub 54 at the point they extend forward from ring 74. Webs 70, flange 72, ring 74 and webs 76 provide structural strength to the outer hub 54. Providing the webs 76 also simplifies the process of forming the outer hub 54.

When the cutting accessory 26 is assembled, outer housing 50 and outer hub 54 are mated together so that the longitudinal axis of window 52 is aligned with one of the webs 76. The coupling assembly employed to hold the cutting accessory 24 to the handpiece allows the rotational orientation of the outer hub 54, and therefore the outer housing 50, to the handpiece to be selectively set. This means one can set the outer hub 54 so that the rotational orientation of the outer housing window 52 relative to the handpiece is selectively set. The alignment of the housing window 52 to one of the hub webs 76 makes it easy for medical personnel to determine the position of the window so its orientation can be set to the desired position.

Outer hub 54 is further formed so that the interior has a number of coaxially extending bores that are centered along the longitudinal axis of the hub. A housing bore 80 extends from the distal end of the hub 54 to a portion of the hub that is subtended by the section that defines the distal most groove 62. The housing bore 80 is the portion of the outer hub 54 in which the proximal end of housing 50 is seated. An inlet bore 82 extends proximally from housing bore 80. The inlet bore 82 has a diameter wider than that of housing bore 80. Inlet bore 82 is subtended by the portion of the hub that defines groove 66. As seen in FIG. 3, laterally extending bore 68 opens into inlet bore 82. A reservoir bore 84 extends proximally from the proximal end of inlet bore 82. The reservoir bore 84 has a diameter greater than that of the inlet bore 82. A counterbore 86 extends distally from the reservoir bore to the proximal end of the outer hub 54. The counterbore 86 has a wider diameter than reservoir bore 84. The outer hub 54 is formed so that the inner walls that define the bores have a short tapered section 88 that defines the transition between the counterbore 86 and reservoir bore 84.

A tubular rotating shaft 90 is disposed inside housing 50. The distal end of shaft 90 is closed. Extending proximally from the distal end, shaft 90 is formed to have a window 93. The window 93 is defined by edge surface 94 formed in the shaft 90. Window 52 of housing 50 is defined by a similarly sharp beveled edge 53 of the housing. Thus, edges 53 and 94 function as scissors when shaft 90 is rotated.

In some preferred versions of the invention, housing 50 and rotating shaft 90 are formed so that window 52 is smaller in size than window 93. For example in one version of the invention, the housing 50 has an outer diameter of 4.0 mm. In this version of the invention, the length of housing window 52 along the longitudinal axis of the window 52 is 0.209 inches. In this version of the invention, the length of shaft window 93 along the longitudinal axis of the window 93 is 0.233 inches. In another version of the invention, housing 50 has an outer diameter of 3.5 mm. In this version of the invention, the length of window 52 along the window's longitudinal axis is 0.175 inches. The length of the window 93 of the complementary shaft 90 is 0.208 inches. In still another version of the invention, housing 50 has an outer diameter of 2.5 mm. In this version of the invention, the length of window 52 formed in the housing is 0.082 inches. The complementary shaft 90 of this cutting accessory 26 has a window 93 with a length of 0.140 inches as measured along the longitudinal axis of window 93.

As seen in FIGS. 5 and 6, it is further observed that the distal end of rotating shaft 90 is formed so that the surface opposite window 93 is a flat surface 98. The shaft 90 is formed so that flat surface 98 extends from a position immediately proximal to where the material forming the shaft starts to curve over the longitudinal axis of the shaft to a position proximal to the space subtended by window 93. Also a small through opening 102 extends from the shaft flat surface 98 into the center void space of the shaft. Opening 102 is positioned so as to be in registration with shaft window 93. Opening 102 is smaller in size than window 93. The Applicant's Assignee's U.S. Pat. No. 6,342,061, SURGICAL TOOL WITH INTEGRATED CHANNEL FOR IRRIGATION, issued Jan. 29, 2002, and incorporated herein by reference, provided additional discussion regarding how the distal end of a cutting accessory may be constructed.

Figure 7A:
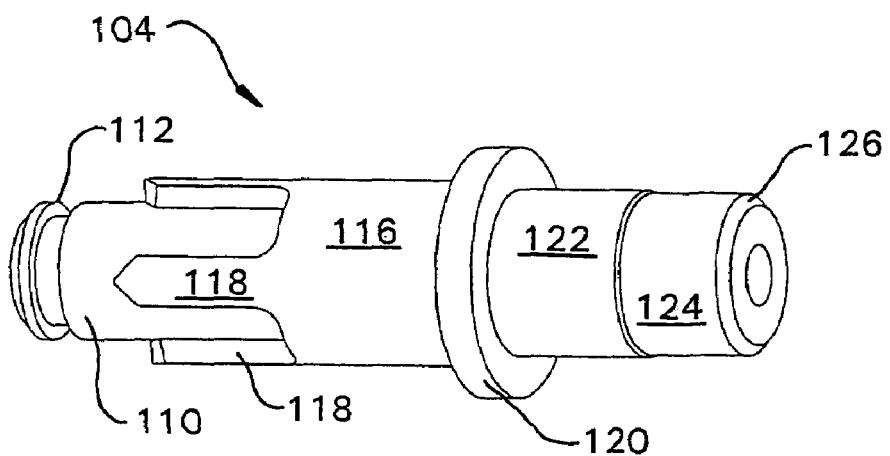
FIGS. 7A and 7B are, respectively, perspective and cross-sectional views of the inner hub of the cutting accessory of this invention.
Figure 7B:
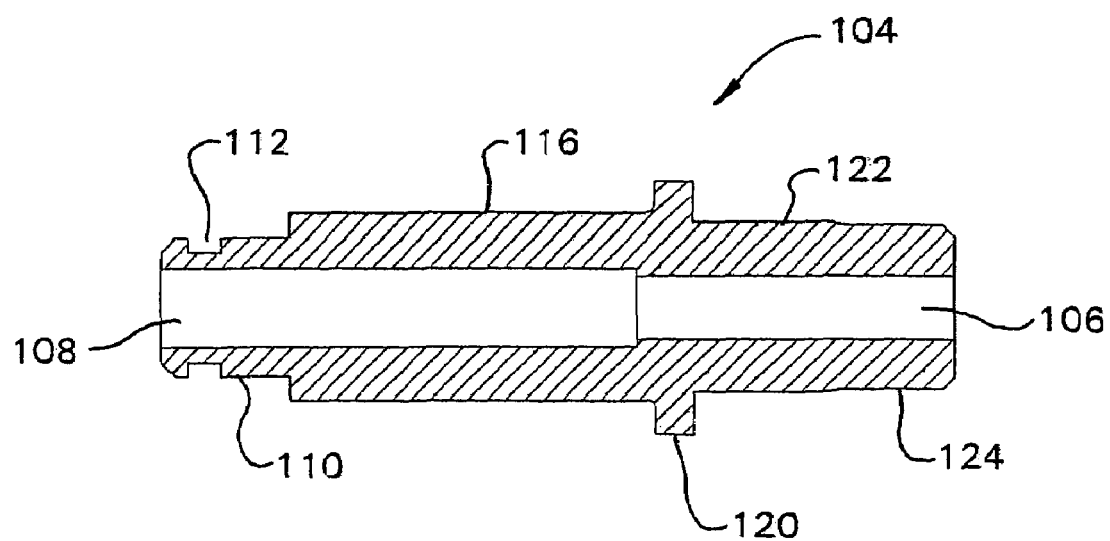

Rotating shaft 90 extends through outer hub 54. An inner hub 104 is fitted to the end of shaft 90 that projects proximally beyond the inner hub 104. As seen in FIGS. 7A and 7B, the inner hub 104 has an axially aligned bore 106 that extends proximally from its distal end. The proximal end of rotating shaft 90 is securely fitted in bore 106. A counterbore 108 that has a larger diameter than bore 106, extends from the proximal end of bore 106 to the proximal end of inner hub 104.

Inner hub 104 is further shaped so that the proximal end has a relatively small diameter stem 110 with a relatively small outer diameter. The proximal end of stem 110 is tapered. Immediately distal to the proximal end, stem 110 is formed to a have a circumferential groove 112. An O-ring 114 (FIG. 3) is seated in groove 112. The inner hub has a main body 116 located distally relative to the stem 110 that has an outer diameter larger than that of the stem. Teeth 118 extend proximally from main body 116 over the stem 110. The inner hub teeth 118 engage complementary teeth connected to the drive shaft of the handpiece motor. A spring 119 is disposed around teeth 118. When the cutting accessory is attached to the handpiece 24, the distal end of the spring seats against a surface associated with the motor shaft. The spring 119 urges the inner hub 104 and rotating shaft 90 forward to accommodate for manufacturing tolerances.

Inner hub 104 is further formed to have a ring shaped flange 120 that is located immediately distal to main body 116 and extends outwardly beyond the main body. Located distally from the flange, 120 there is a neck 122. Inner hub 104 is dimensioned so that neck 122 is inwardly spaced a small distance from the outer hub counterbore 86 so that neck 122 can freely rotate in the counterbore 86. Extending distally from neck 122, the inner hub is formed to have a head 124 that has a diameter less than that of the neck 122. Head 124 is dimensioned to have a diameter so that it is inwardly spaced a small distance from the outer perimeter of the outer hub reservoir bore 84. The inner hub 104 is further shaped so that there is a small bevel 126 around the outer perimeter of the distal end of head 124.

Prior to the insertion of the rotating shaft 90 into housing 50, an O-ring 130 (FIG. 3) is fitted over the rotating shaft 90. The O-ring 130 is positioned against the distally directed face of inner hub head 124. More particularly, the components of this invention are dimensioned so that the inner diameter of the unexpanded O-ring is slightly less than the outer diameter of rotating shaft 90. Generally, the inner diameter of the O-ring 130 is between 0.002 and 0.005 inches less than that of the rotating shaft 90, in some versions of the invention, this difference is approximately 0.003. The outer hub 54 is shaped so that the reservoir bore 84, the space in which the O-ring is seated, has a diameter that is less than outer diameter of the O-ring when the O-ring is in on-the-shaft expanded state. Typically, these components are selected so that the on-the-shaft expanded state outer diameter of the O-ring 130 is 0.007 to 0.010 inches greater than that of the reservoir bore 84. Thus upon the insertion of the rotating shaft-inner hub-O-ring assembly into the outer housing-outer hub assembly, the O-ring 130 becomes a static seal around the rotating shaft 90.

The outer hub reservoir bore 84 and counterbore 86, the inner hub neck 122 and head 124 and O-ring 130 are further dimensioned so that, when the distal end of the inner hub 104 is fitted in the proximal end of the outer hub 54, there is a small amount of free space between the O-ring and the distally located base of the reservoir bore 84. In the event O-ring 130 does creep distally, the movement is eventually stopped by the abutment of the O-ring against the step between the reservoir bore 84 and the inlet bore 82.

In versions of this invention designed for ENT surgery, the maximum outer diameter of the housing 50 is typically 5.0 mm or less. In other versions of the invention designed for ENT surgery, such as sinus surgery, the outer diameter of the housing 50 is 4.5 mm or less. In more preferred versions of the invention designed for this type of surgery, the outer diameter of the housing is 4.0 mm or less. Sometimes, ENT/sinus surgery is performed using cutting accessories that have housings with outer diameters of 3.5 mm or less. In one version of the invention, housing 50 has an outer diameter of 0.1345 inches and an inner diameter of 0.1125 inches. The complementary rotating shaft 90 has an outer diameter of 0.099 inches. Generally, in order to have sufficient flow of irrigating solution to the distal end of the cutting accessory, the minimum separation between the inner wall of the housing 50 and the outer wall of the rotating shaft 90 should be at least 0.0005 inches. Flat surface 98 is formed so as to extend a depth of up to 50% of the wall thickness of the rotating shaft. The actual distal end of the rotating shaft in which window 93, opening 102 and most of flat surface 98 are formed may be a separate component from the proximal portion of the shaft.

The structure of one specific handpiece 24 designed to actuate cutting accessory 26 is now described by reference to FIGS. 8A, 8B and 8C. The handpiece 24 has an elongated body 134 in which motor 38 is housed. The front end of body 134 is formed with an opening 135 for receiving substantially all of the outer hub 54 and the whole of the inner hub 104. Motor 38 has a cannulated shaft 136 through which fluid is flowed to and from the center of the rotating shaft 90. A suction fitting 138 extends from the proximal end of body 134. Suction fitting 138 is axially aligned with and in fluid communication with rotating shaft 90 and the cannulated motor shaft 136. Suction is drawn through fitting 138 from a suction pump 137 (FIG. 1) through a suction line 139. Means of assembling a handpiece having this construction is disclosed in the Applicants' Assignee's U.S. Pat. No. 6,152,941, ENDOSCOPIC CANNULATED HANDPIECE MOTOR WITH INTEGRATED SUCTION CONTROL, issued Nov. 28, 2000 incorporated herein by reference.

Irrigating solution is introduced into the handpiece 24 through an inlet fitting 140 attached to the proximal end of body 134. The body is formed with a set of irrigation conduits, generally identified as 142 that extend from fitting 140 towards the distal end of the body. The most distal portion of conduit 142 extends to a discharge opening 144 formed in an interior wall of the body that defines opening 135. The body 134 is formed so that, when the cutting accessory 26 is seated in opening 135, discharge opening 144 is in registration with groove 66.

A valve 146 is rotatably mounted in a valve bore 148 formed in the body between the cannulated motor shaft 138 and the suction fitting 136. A branch of conduit 142 extends to the valve bore 148. Valve 146 is selectively positioned by a slide switch 147 located adjacent the distal end of the body 134. The valve 146 is selectively positioned to: place the cannulated motor shaft and rotor shaft in communication with the suction fitting; or place the rotor shaft in fluid communication with the conduit 142 through which irrigation fluid is introduced into the handpiece 24. A discussion of how valve 146 is selectively positioned is contained in the Applicants' Assignee's U.S. patent application Ser. No. 09/302,148, POWERED SURGICAL HANDPIECE WITH INTEGRATED IRRIGATOR AND SUCTION APPLICATION filed Apr. 29, 1999, now U.S. Pat. No. 6,689,146 and the Applicants' Assignee's U.S. patent application Ser. No. 10/251,646, SURGICAL TOOL SYSTEM filed Sep. 21, 2002, now 6,958,071 both of which are incorporated herein by reference. It should be understood that this flow of fluid through the rotating shaft 90 is sometimes referred to as a purge flow. The flow is provided to clear debris that may be trapped within the rotating shaft 90.

One pump 44 that can be used to supply irrigation fluid to the handpiece is the TPS™ Irrigation Console Pump, manufactured by the Applicant's Assignee, the Stryker Corporation of Kalamazoo, Mich. This particular pump is capable of supplying between 22 and 41 ml/min of irrigating solution to the handpiece at a pressure of 16 psi. It is believed that, in preferred versions of practicing the method of this invention, pump 44 is set to deliver at least 25 ml/min of irrigating solution, in more preferred versions of the invention, the pump is set to deliver at least 30 ml/min. of fluid.

The system 20 of this invention is used to perform endoscopic surgery such as the sinus surgery depicted in FIG. 1. When surgery is employed using this system, the endoscope 32 is positioned near the surgical site in order to allow the surgeon to view the site. The cutting accessory 26 is positioned at the surgical site in order to perform the desired surgical procedure. Typically, the procedure involves actuating the rotating shaft 90 so that the cutting accessory 26 can be employed to selectively remove the tissue and/or shape the tissue in the patient. The system 20 of this invention is employed to perform surgery in a "dry" environment, that is, at a surgical site that has not been flooded, immersed, in an irrigating solution. One such environment is the nasal passages in which the system is placed in order to perform sinus surgery.

Pump 44 forces irrigating solution to the distal end of the cutting accessory 26. Specifically, the fluid flows through a supply line 146 that extends from the outlet of the pump to the handpiece inlet fitting 140. The fluid flows through conduit 142 and is discharged through opening 144 in the handpiece. If the outer hub bore 68 is in registration with the handpiece opening 144, the irrigating solution is essentially discharged directly into bore 68. If, however, the outer hub bore 68 is not in registration with the handpiece opening 144, the fluid flows in groove 66. Outer hub O-rings 64 serve as seals that prevent the fluid from flowing outside of the space between the O-rings. In a very short amount of time, the backpressure forces the fluid in groove 66 through the outer hub bore 68.

The irrigating solution flows through from bore 68 into the inlet bore 82 and reservoir bore 84 internal to the outer hub 54. The O-ring 130 functions as a static seal around rotating shaft 90. The O-ring 130 thus prevents the irrigating solution introduced through bore 68 from flowing proximally beyond the reservoir bore. Consequently, a reserve of fluid is built up in both the inlet bore 82 and the reservoir bore 84. Thus, the pressure forces substantially all, if not all, the fluid introduced into the outer hub 54 downstream towards the distal end of the cutting accessory 26. The fluid flows in the annular space between the inner wall of the housing 50 and the outer wall of the rotating shaft 90. There is, it should be understood, a relatively wide separation between these two surfaces in the vicinity of rotating shaft flat surface 98. The interstitial space between these two surfaces functions as a reservoir in which irrigating solution is held.

Eventually, the fluid flows to the distal end of the cutting accessory housing 50. The suction drawn through rotating shaft 90 draws the fluid through the shaft window 93 and opening 102. Owing to the suction, the fluid flows proximally through the rotating shaft 90 and the handpiece 24. When the irrigating solution flows through these components, it functions as transport media that forces the debris drawn into the rotating shaft 90 to the collection receptacle associated with the suction pump.

Figure 9:
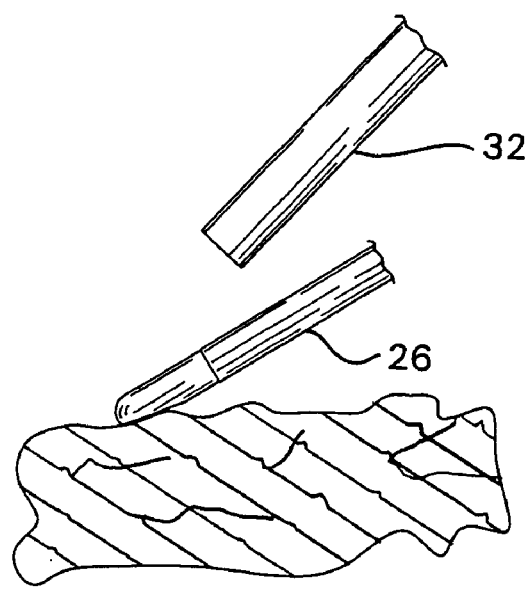
FIG. 9 depicts how the cutting accessory of the surgical system of this invention is employed to perform a surgical procedure.

The system is used to perform a surgical procedure as illustrated in FIG. 9. As seen here, in order to employ the cutting accessory 26 to remove tissue, the accessory is positioned so that housing window 52 is pressed against the tissue. The actuation of the handpiece motor 38 results in the rotation of rotating shaft 90 and the resultant cutting of the tissue. The excised tissue is drawn through the cutting accessory 26 and the handpiece 24 as discussed above. As seen in this Figure, the distal end of the endoscope 32 is positioned adjacent the surgical site to which the cutting accessory is applied so that the surgeon can view the procedure.

When the method of surgery of this invention is practiced, the cutting accessory simultaneously performs four functions. First, as a consequence of the rotation of the shaft 90, the cutting accessory 26 functions as a cutting unit so that tissue, such as the outer surface of the sinus lining, is excised.

Figure 10:
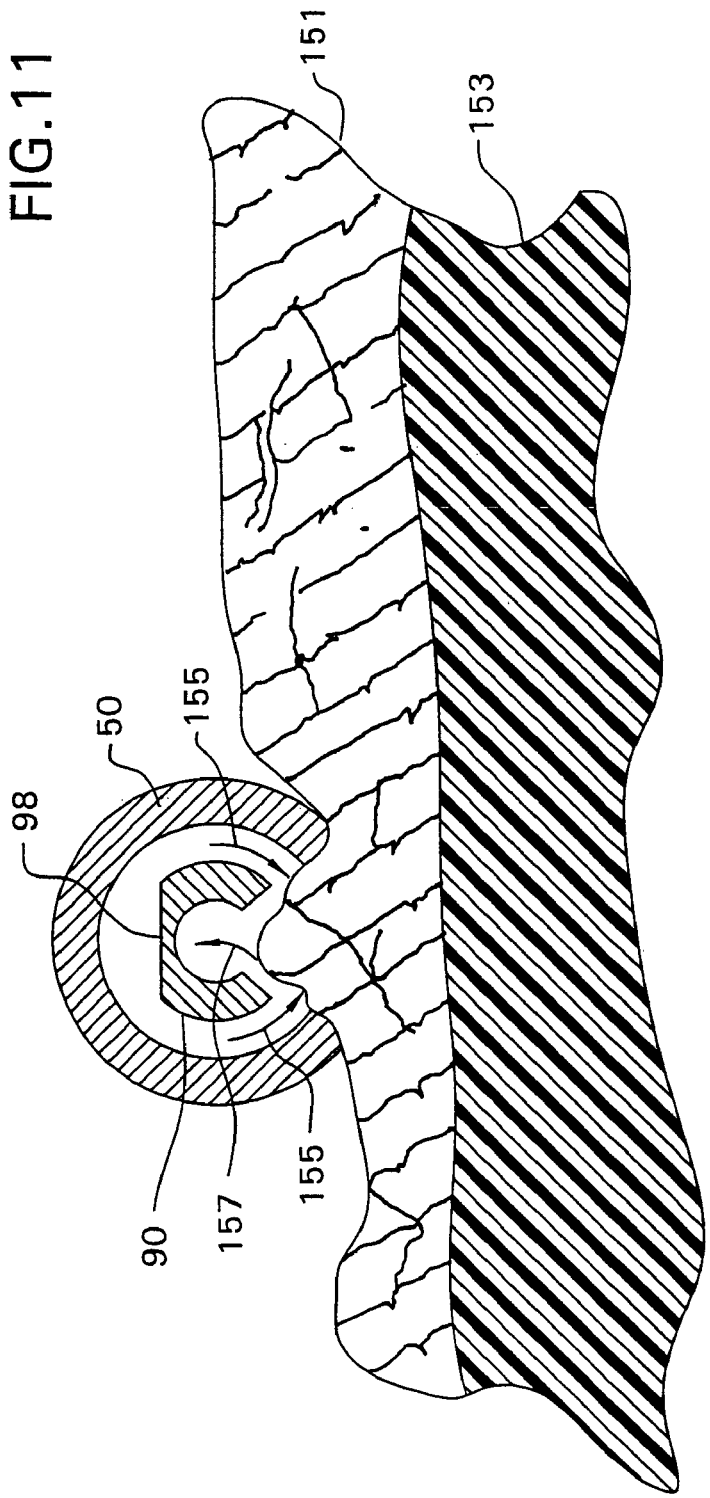
FIG. 10 is a cross-sectional view along line 10-10 of FIG. 9 depicting the fluid flow patterns between the cutting accessory of this invention and the tissue against which the accessory is applied.

Secondly, irrigation fluid is discharged onto the tissue as it is being excised. One path through the cutting accessory 26 through which fluid is discharged is illustrated in FIG. 10. As seen here, the fluid which is under pressure, as represented by arrows 155, flows in the arcuate gaps between the rotating shaft 90 and housing 60 and out through window 52. This discharge is due, in part, to the seal affect of hub O-ring 130. This O-ring 130 substantially, if not completely, blocks any proximal flow of irrigating solution that might otherwise occur when the fluid enters the interior of housing 50 through hub bore 68. More particularly, in some versions of the invention, O-ring 130 provides a sufficient seal to ensure that at least 90% of the irrigating solution introduced into cutting accessory bore 68, flows to the distal end of the cutting accessory 26. In more preferred versions of the invention, the O-ring 130 provides a sufficient seal so that at least 95% of the solution introduced into the cutting accessory flows to the distal end of the accessory.

Moreover, when the rotating shaft 90 is seated in the housing 50, the distal end tip of the shaft abuts against the adjacent inner wall of the housing, as depicted by FIG. 13. Consequently, inside the housing there is a small circular blockage immediately above the distal end of the rotating shaft. This blockage inhibits the flow of irrigating solution. Consequently, when the fluid approaches the distal end of housing 50, it is under a significant amount of pressure. The solution is therefore discharged from either side of the interior of the housing 50 outwardly through window 52 along a path of travel that is angularly offset to the longitudinal axis of the cutting accessory and towards the proximal end of the cutting accessory This fluid functions as a lubricant between the tissue and the edge surfaces of the housing and shaft. The decreased friction of the tissue moving against the metal surfaces of the cutting accessory lessens the extent to which the tissue is pinched between the housing and the shaft. This results in a relatively clean, sharp cut of the tissue, sinus lining 151 in FIG. 10. This sharp cutting action thus reduces the pinching, the drawing in, of the tissue immediately outside the housing window into the cutting accessory. The reduction of this pinching thus lessens the extent to which the tissue the surgeon wants left at the surgical site is unintentionally removed. Thus, when sinus surgery is performed using the method of this invention, the extent to which tissue that should remain at the surgical site is inadvertently excised from the site is reduced. In this sinus surgery, this helps ensure that the sinus lining 151 is not removed to the extent that portions of the underlying bone 153 are left exposed.

The third function performed by the cutting accessory simultaneously with the other two is the drawing of the irrigating solution discharged at the surgical site away from the site. This fluid flow is represented by arrow 157 in FIG. 10. This action occurs as a result of the application of the suction to the surgical site through the distal end window of the rotating shaft. This suction minimizes the extent to which the discharged irrigating solution is released at the surgical site. This fluid, if it remains uncollected, can complicate the performance of the surgical procedure.

The fourth function performed by the cutting accessory 26 is the circulation of the irrigating solution through the cutting accessory so that it serves as transport media for debris drawn into the rotating shaft. This function is represented by arrow 159 of FIG. 14 that depicts the fluid flow from between the housing 50 and shaft 90 through window 102 so that there is fluid flow down the shaft.

The discharge of irrigating solution by the cutting accessory while the accessory is used to perform a surgical procedure has still other advantages. Specifically, the system of this invention delivers a relatively large quantity of fluid to the distal end of the cutting accessory. Substantially all this fluid is normally drawn back proximally through the rotating shaft 90. Consequently, this fluid forms a relatively powerful pressure head. This pressure head serves to force debris downstream in the cutting accessory that could possibly inhibit the suction flow.

There may, however, be instances in which debris in the cutting accessory or handpiece do partially, but not completely, block the suction flow. If this event occurs, the irrigating solution will start to pool in the vicinity of the surgical site. The surgeon immediately observes this pooling and is able to interpret it as an indication that there is partial clogging of the cutting accessory 26. Upon recognizing that this is the situation, the surgeon is able to withdraw the cutting accessory in order to clear the clog and/or insert a new, unclogged accessory. Thus, the method of this invention provides a means for a surgeon to quickly determine if the cutting accessory is partially clogged and that such clog is reducing the overall efficiency with which the surgical procedure is being performed.

Figure 12:
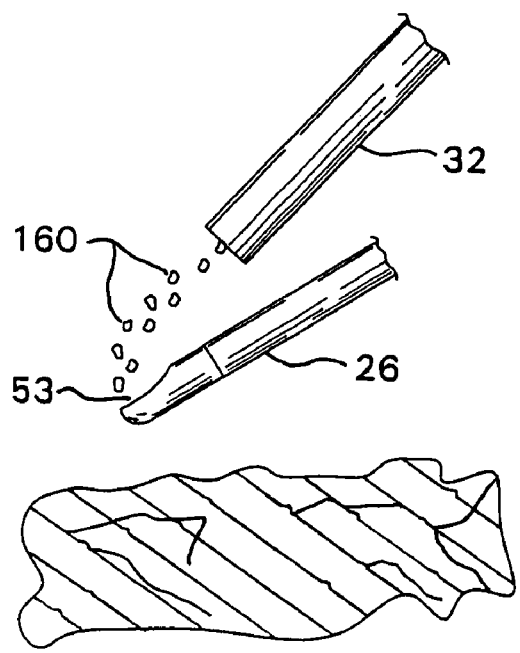
FIG. 12 depicts how the cutting accessory of the surgical system of this invention is employed to remove debris from the distal end of the endoscope of the system.
Figure 11:
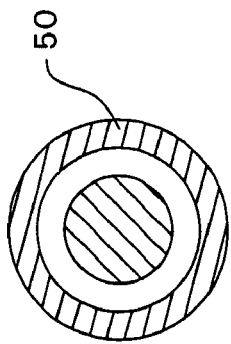
FIG. 11 depicts a means by which water is discharged from the distal end of the cutting accessory.

Moreover, as a consequence of the procedure being performed, debris may strike and adhere to the distal end of the endoscope 32. These debris often obstruct the surgeon's view of the surgical site. In the system of this invention, the debris are cleaned from the endoscope by positioning the cutting accessory and endoscope as illustrated in FIG. 12. Specifically, the cutting accessory 26 is rotated so that housing window 52 is oriented away from the tissue the accessory is used to work. The distal end of the endoscope 32 is placed in relatively close proximity to the housing window 52. In some preferred methods of practice, the distance is a maximum of 5.0 cm away from the housing window, in other versions of the invention, this distance is a maximum of 3.0 cm away from the housing window. In preferred versions of the invention this distance is a maximum of 2.0 cm away from the housing window. In still more preferred versions of the invention, this distance is a maximum of 0.5 cm away from the housing window. When the cutting accessory 26 is so positioned, fluid is discharged in pulses as a spray through the housing window. In the drawings, the pulses of fluid are represented as droplets 160. Owing to the position of the components, some of the droplets splash against the distal end of the endoscope so as to wash off debris that have adhered to the endoscope. This removal of the debris cleans the endoscope so that the vision through it is again unobstructed.

Two mechanisms which are believed to cause the pulse discharge or irrigating solution from the cutting, accessory 26 are described by reference to FIGS. 13 and 14. First, it should be understood that one reason the pulse flow is present is that because substantially all, if not all, irrigating solution that is introduced into the outer hub through bore 68 is flowed downstream. Little, if any, irrigating solution, leaks distally beyond O-ring 130. Consequently, fluid that reaches the distal end of the housing is under a relative high amount of pressure. In order to achieve these pressures, pump 44 is operated to force fluid into the handpiece 24 and cutting accessory 26 at flow rates between 25 and 112 ml/min at pressures between 7 and 32 psi. It should, of course, be recognized that the actual fluid pressure is also based on the speed of pump 44, which can typically be set by the surgeon.

It should further be understood that the minimum rate at which irrigating solution is supplied to the pump is a function of the suction drawn by pump 137. Generally, the higher the rate of the suction that is drawn, the higher the rate solution is supplied to the cutting accessory 26. For example, when a relatively low suction is drawn, 3 inches Hg, solution is supplied to the cutting accessory at a flow rate of a minimum of 25 ml/min and, more preferably, at least 30 ml/min in order to obtain the desired pulse flow discharge from outer housing window 52. When a suction of 14 inches Hg is drawn from the surgical site by pump 137, solution should be flowed to the cutting accessory at a minimum rate of 40 ml/min to practice this invention and more preferably, a minimum rate of 60 ml/min. Generally, the maximum rate at which it is anticipated solution will be flowed to the cutting accessory is 90 to 120 ml/min. Generally, the irrigating solution is flow to the cutting accessory at a pressure of approximately 16 psi.

FIG. 13 illustrates one instance when the cutting accessory of this invention discharges a pulse of fluid. Specifically, as seen by this Figure, in each rotation of shaft 90, flat surface 98 comes in registration with housing window 52. A relatively large volume of fluid is located immediately above the flat surface 98. Given the pressure this fluid is under, the exposure of this quantity of fluid to the window 52 causes the discharge of this fluid from the window 52, as represented by arrow 162.

In FIG. 13, arrow 162 shows the fluid flow as being directed, proximally, back towards the end of the cutting accessory 26 connected to surgical handpiece 24. Fluid flows in this direction because, prior to surface 98 coming into registration with housing window 52, the solution held over surface 98 is highly pressurized. When surface 98 initially comes into registration with window 52, the irrigating solution over the distal end of the surface, given its highly pressurized state, is believed to momentarily form a blockage that prevents upstream fluid from continuing to flow distally. This blockage essentially forms a surface, represented by phantom line 163, off which the upstream fluid is reflected and therefore directed proximally. This blockage is believed to exist even though a small amount of fluid is drawn immediately into the rotating shaft 90 through window 102.

It should be further understood that the spray of irrigating solution is not just directed proximally. The solution is also dispersed over an arcuate area above the cutting accessory 26. This arcuate dispersal occurs because, as the solution is being discharged, rotating shaft flat 98 is rotating across window 52. Consequently, the fluid is discharged with the angular momentum of the rotating shaft 90 through outer housing window 52. This discharge it should be understood is in the form of a pulse. Collectively, the pulsed discharges represent at least 50% of the volume of irrigating solution that is discharged of the irrigating solution from the cutting accessory 26 when this invention is employed.

Fluid is also believed to be pulsed from the cutting accessory 26 when shaft window 93 goes into registration with housing window 52 as seen in FIG. 14. Again, owing to the pressure to which the fluid located on surface 98 is exposed, when this fluid, through shaft opening 102, shaft window 93 and housing window 52 is exposed to the outside environment, it is rapidly expelled through these openings, as represented by arrow 164.

As a consequence of the sealing function performed by O-ring 130, an appreciable percentage of the fluid that is supplied to the cutting accessory is discharged through window 52 before being drawn back into the accessory by suction pump 137. Depending on the actual rate the system 20 is configured to operate, at least 6% of the solution introduced through into the cutting accessory is discharged through window 52, in preferred versions of the invention, at least 8% of the solution is so discharged and, in still other versions of the invention, at least 10%, or at least 16%, of the solution is so discharged. More particularly, when solution is introduced into the cutting accessory at a rate of 25 ml/min, solution is discharged through window at rates of 2 ml/min or more, and often 4 ml/min. or more. When solution is introduced into cutting accessory at rates of between 40 to 60 ml/min, fluid is discharged through window 52 at a rate of at least 4 ml/min and, in more preferred versions of the invention, at a rate of at least 10 ml/min. Generally, the maximum rate at which the irrigating solution should be discharged when ENT/sinus surgery is performed is 15 ml/min.

The system and method of this invention offers a number of benefits that enhance the efficiency of nasal passage, sinus cavity and throat surgical procedures, such as those performed on the sinus lining. In the method of this invention, irrigating solution is discharged by the cutting accessory on the surgical site while the accessory is being used to remove tissue. This facilitates the sharp removal of the tissue that is to be removed while minimizing the extent to which excess tissue is removed. During the exact times the cutting accessory is being used to remove tissue, this system and method provide a simple means for a surgeon to quickly determine whether or not there is a partial clog in the cutting accessory. The system and method of this invention also provide a means for a surgeon to clean the endoscope 32 used to perform the procedure without having to withdraw the endoscope from the surgical site or introduce additional instrumentation into a small surgical field.

It should further be understood that the another feature of the system and method of this invention is that it is only necessary to pump a relatively small amount of irrigating solution into the cutting accessory 26 in order to pulse discharge the solution from outer housing window 52. This is because O-ring 130 ensures that substantially all, if not all, solution that is introduced into outer housing hub inlet bore 68 flows distally; the fluid is not drawn proximally by the suction force back into the handpiece. Consequently, when the low suction, 3 inches Hg, is drawn it is generally necessary to flow the irrigating solution into the pump at a relatively low rate, 25 ml/min, before the solution is discharged from window 52. Since the solution is introduced into the cutting accessory 26 at a relatively low flow rate, and since a maximum of 20%, often 17% or less and sometimes 15% or less of the solution is actually discharged from the outer housing window 52 to the surgical site, only a relatively small quantity of solution is so discharged.

The relatively low volumetric discharge of solution serves to minimize, if not eliminate, the flooding in the body passageway to which the surgical tool of this invention is applied and the attendant adverse consequences to the patient. This discharged solution, it should be understood is, for the most part, if not entirely, drawn back into the handpiece through the suction applied to rotating shaft 90. Thus, the system and method of this invention introduces into an otherwise non-fluid filled passageway a quantity of irrigating solution that improves the efficiency of the surgical procedure and that does not risk the patient.

Figure 15:
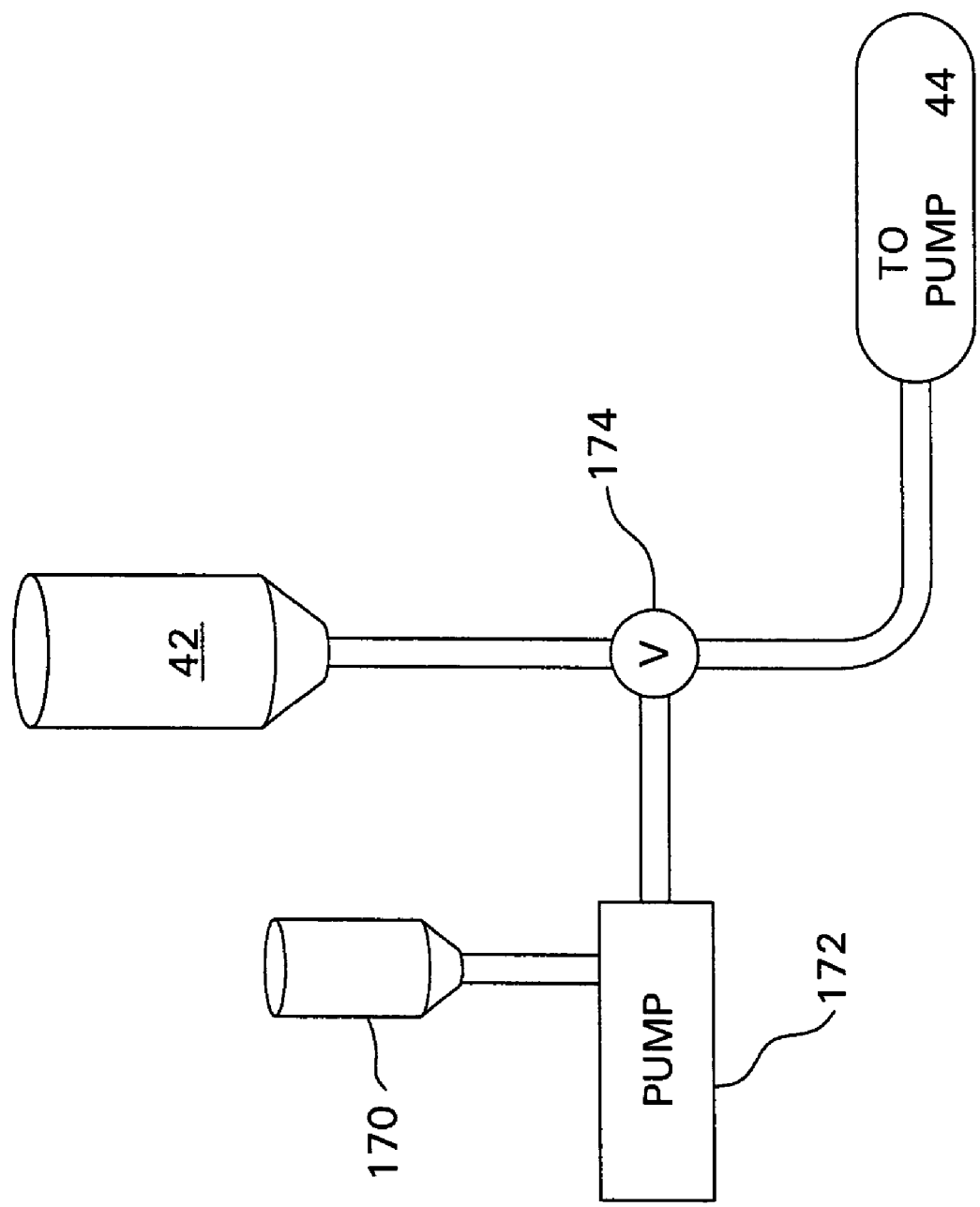
FIG. 15 is a block diagram that depicts how the system of this invention is provided with equipment for topically supplying medicine to a surgical site.

The system 20 of this invention can also be used to apply medicine or other supplemental compound topically, directly to the surgical site. Types of medicines or supplemental compounds that can be applied to the surgical site include, but are not limited to: antibiotics; anti-inflammatories; anti-fungal compounds; and anesthetics. Other compounds that can be applied include lubricants that, when applied to the surgical site, facilitate the cutting of the tissue or lubricants that reduce the friction between the debris and bone fragments and the components forming the suction path. Clearly, multiple compounds and medicines may be simultaneously introduced. As seen by FIG. 15, this version of the system is provided with a container 170 of medicine or other supplemental compound that is located between container 42 and pump 44. The contents of container 170 are forced into the feed line to pump 44 by an auxiliary pump 172. Auxiliary pump 172 is any convenient device for injecting a controlled volume of fluid into the feed line. For example, one form of pump 172 may be an electronically controlled plunger. Medicine in container 170 is flowed into the housing in which the plunger is seated when the plunger is retracted. Then, in response to an actuation signal, the plunger is forced into the housing so as to force a select volume of medicine into the feed line to pump 44. In these versions of the invention, an electronically set valve 174 regulates the flow of fluid from the auxiliary pump 172 to the feed line. This prevents the medicine from flowing downstream when its application is not required.

In this version of the invention, the actuation of pump 172 and valve 174 are regulated by circuitry internal to the control console 40. When application of medicine is desired, valve 174 is first opened. The auxiliary pump 172 is then actuated to force the downstream flow of the medicine so that it mixes with the irrigating solution supplied to the cutting accessory 26. The surgeon then applies the medicine to the tissue the same way irrigating solution is applied to the tissue using the cutting accessory 26.

It should be recognized that the foregoing description is limited to specific versions of the system and method for performing endoscopic surgery. Other versions of the invention may vary from what has been described. For example, the specific structures of the handpiece 24 and cutting accessory 26 may vary from what has been described. Also, it should be understood that the illustrated cutting accessory 26 is a specific type of cutting accessory, a shaver. The invention may be practiced with different types of cutting accessories, for example, burs or rasps. Moreover, while the illustrated cutting accessory edges 53 and 94 are straight, in some versions of the invention they may be formed with teeth. Similarly, it should be understood that the cross section geometry of both the housings and moving shafts of alternative cutting accessories of this invention may vary from the circular profile of the described accessory. For instance, in other versions of the invention, these components may have curved but non-circular cross sectional profiles. In still other versions of the invention, these components may have linear cross sectional profiles. For example, these components may have polygonal cross sectional profiles, for example, rectangular, pentagon or hexagon profiles.

It is understood that a conventional bur or rasp type cutting accessory will have an open ended outer housing. It is contemplated that, in some versions of these accessories designed for the present invention, the end of the outer housing may be partially closed. A window larger than window 52 provides access to the cutting head. This allows the pressurized volume of irrigating solution to build up so, when the rotating shaft flat over which the fluid is held comes into registration with the window, the fluid is forcefully discharged as a pulse out of the window.

Moreover, it should likewise be recognized that, in some versions of the invention it may not be necessary to provide the rotating shaft 90 of the cutting accessory 26 with window 102. For example, it may not always be necessary to provide this window in versions of the invention where the handpiece is capable of directing a purge flow of irrigating solution to the distal end of the cutting accessory through the cutting accessory rotating shaft 90.

Similarly, the described and illustrated surface features of the outer hub 54 and inner hub 104 should be understood to be illustrative and not limiting. In versions of this invention designed for use with alternative coupling systems, hubs 54 and 104 may have different surface features to facilitate their coupling to the complementary handpiece and drive unit internal to the handpiece.

It should similarly be recognized that, in other versions of the invention, the shaft integral with the cutting accessory may not rotate, it may reciprocate back and forth. A rasp is one type of cutting accessory that has a reciprocating shaft. Typically, the handpiece used to actuate a cutting accessory with a reciprocating type shaft has a linkage assembly capable of transferring the rotary movement of the motor's shaft into a back and forth motion for application to the cutting accessory shaft. Alternatively, this linkage is contained in an attachment that is fitted to the distal end of the handpiece. In some versions of the invention, the shaft may be part of a linkage assembly that causes an actual cutting head to engage in sagittal, repetitive back-and-forth movement.

It should likewise be understood that the shapes of the components forming this invention may likewise vary from what has been described. For example, in some versions of the invention, the distal ends of the housing and rotating shaft of the cutting accessory may be shaped to have diameters less than the more proximal sections of these components. Also, it should be recognized that not all cutting accessories integral with this invention will include a motor-driven rotating shaft inside a static housing. In other versions of the invention, the cutting accessory may include a tissue working member that emits RF energy, a cauterizing probe, a member that emits ultrasonic energy or a member that emits light energy such as a coherent, laser, light. In these versions of the invention, the actual accessory applied to the site would have an elongated member that contains a tip with an energy emitting device or a conduit through which the energy emitted by the handpiece is applied to the device. The accessory would be formed to define a lumen through which irrigating fluid is discharged to the surgical site. There would also be a lumen through which suction is drawn from the surgical site. In some embodiments of these versions of the invention, a single lumen or conduit may perform two or more of the above functions. Thus, with a single instrument, the surgeon is able to apply RF energy, ultrasonic energy or light energy to a surgical site, provide fluid in order to clean the endoscope or disperse medication, and draw a suction to remove the fluid and severed material from the site.

It should likewise be realized that, in some versions of the invention, cutting accessories that are manually operated, such as pinchers, may be provided with the irrigation and suction features of this invention.

Moreover, there is no requirement that, in all versions of the invention irrigating fluid be supplied to the surgical site through the annular channel between the outer housing and the moving shaft. In some versions of the invention, it may be desirable to provide the cutting accessory with a lumen that has a circular cross sectional profile that is parallel to the conduit defined by the rotating shaft. This lumen is defined by a supplemental tubular structure integral with the outer housing. The irrigating fluid is supplied to the surgical site through this lumen.

Similarly, it should be recognized that not all handpieces incorporated into the system of this invention or employed in its method may be designed so as to, upon fitting of the cutting accessory to the handpiece, affect a coupling of an irrigation supply line to the cutting accessory. In other versions of this invention, it may be necessary for the surgeon to make this connection manually. Also, alternative handpieces of this invention may not have electronically actuated motors. In an alternative version of the invention, a handpiece may have a pneumatically driven motor.

Also, it should be understood that the system and method of this invention may be used to perform other types of surgeries than nasal, sinus and throat surgeries. There may be other types of surgeries that are performed at dry surgical sites, that is, surgical sites that are immersed in an irrigating solution at which the efficiencies gained by the system and method of this invention may be useful. Other types of surgeries with which the system and method of this invention may be employed include laryngeal tracheal and vocal cord surgery. The system and method of this invention may also be employed in certain types of reconstructive and cosmetic surgery including lypoplasty.

Furthermore, additional components may be provided in alternative versions of this invention. For example, volumetric flow meters may be attached to both the line 46 through which irrigating solution is applied to the handpiece 24 and line 139 through which suction is employed to remove this fluid as well as any entrained debris. In this version of the invention, the volumetric flow rates through these tubes are monitored. In the event a comparison of these flow rates indicates more fluid is being discharged at the surgical site than is being drawn off, the control console may actuate an alarm. This alarm would give the surgeon an indication that, given the difference in flow rates, there may be a possibility of a blockage in the suction flow path.

It should further be recognized that not all medicines and supplemental compounds introduced to the surgical site in accordance with the method of this invention are liquid state. In alternative versions of the invention, suspended dry compounds may be introduced by mixing the compounds in the irrigating solution.

Therefore, it is the intention of the appended claims to cover all such modifications and variations that come within the true spirit and scope of this invention.

What is claimed is:

1. A method of performing surgery on a site within a dry passageway, said method including the steps of:

positioning an endoscope in the passageway, the endoscope having a distal end, wherein the distal end of the endoscope is positioned so that a surgical site in the passageway can be viewed through the distal end of the endoscope;

placing an elongated cutting accessory in the passageway, the cutting accessory having a distal end with a tissue working member and the cutting accessory defining a conduit through which fluid is discharged from the distal end of the cutting accessory;

viewing the surgical site and the cutting accessory through the endoscope;

applying the cutting accessory to the surgical site and performing a procedure with the cutting accessory;

cleaning the distal end of the endoscope by:

causing fluid to flow through the conduit so that the fluid is discharged from the distal end of the cutting accessory in a spray; and positioning the endoscope and the cutting accessory so that the fluid spray discharged by the cutting accessory strikes the distal end of the endoscope while the distal end of the endoscope is in the passageway; and drawing a suction through the cutting accessory to remove from the passageway the fluid discharged to clean the endoscope.

2. The method of claim 1 wherein the passageway in which the endoscope and cutting accessory are inserted is a one consisting from the group of: sinus passageway; nasal passageway; and throat.

3. The method of claim 1 wherein the cutting accessory consists of a moving shaft that is disposed inside an outer housing and:
   said step of performing the procedure includes moving the shaft relative to the outer housing; and
   said step of causing the fluid flow is performed by flowing fluid out through the outer housing in an interstitial space between the moving shaft and the cutting accessory.

4. The method of claim 3 wherein:
   the powered surgical handpiece includes a motor and the moving shaft is connected to the motor; and
   said step of moving the shaft is performed by actuating the handpiece motor.

5. The method of claim 1 wherein the cutting accessory consists of a tubular moving shaft that is disposed inside an outer housing and:
   said step of performing the procedure includes moving the tubular shaft;
   said step of causing the fluid flow is performed by flowing fluid out through the outer housing in an interstitial space between the moving shaft and the cutting accessory; and
   said step of drawing a suction is performed by drawing a suction through the moving tubular shaft.

6. The method of claim 5 wherein said step of performing the surgical procedure is performed by rotating the tubular shaft.

7. A method of performing surgery in a sinus passageway, a nasal passageway or a throat, said method comprising the steps of:
   positioning a cutting accessory in the sinus passageway, the nasal passageway or the throat, the cutting accessory having:
      an elongated outer housing with opposed proximal and distal ends, an inlet bore in the proximal end and an outlet opening adjacent the distal end; and
      an elongated tubular moving shaft within the outer housing, the moving shaft having opposed proximal and distal ends, a tissue working member attached to the distal end and an opening adjacent the distal end;
   applying the cutting accessory to a surgical site to perform the surgical procedure, wherein, in said step, the outer housing distal end and the tissue working member are directed towards tissue at the surgical site;
   simultaneously with said actuation of the moving shaft, drawing a suction from the moving shaft distal end through the moving shaft so that, when the cutting accessory is applied to the surgical site, an irrigating solution is drawn through the moving shaft distal end opening;
   actuating the moving shaft to perform a surgical procedure on tissue to which the cutting accessory is directed;
   simultaneously with said actuation of the moving shaft, flowing the irrigating solution through the outer housing inlet bore and an interstitial space between the cutting accessory outer housing and the moving shaft to the outer housing, wherein solution is flowed through the outer housing at a rate of at least 25 ml/min;
   and providing a seal between the outer housing and the moving shaft, the seal being located between the outer housing inlet bore and distal end of the moving shaft so that the seal blocks at least 90% of the fluid introduced into the interstitial space between the outer housing and the moving shaft from flowing to the proximal end of the moving shaft,
   wherein the rate at which irrigating solution is flowed into the outer housing inlet bore and the rate at which said suction is drawn are set so at least 6% of the solution flowed into the outer housing inlet bore is discharged from the outer housing outlet opening to the surgical site.

8. The method of claim 7 wherein, in said step of actuating the moving shaft, the moving shaft is rotated relative to the outer housing.

9. The method of claim 7 wherein:
   the cutting accessory is attached to handpiece, the handpiece having a suction passageway that is in fluid communication with the proximal end of the moving shaft;
   said step of drawing a suction through the moving shaft is performed by drawing a suction through the suction passageway in the handpiece.

10. The method of claim 9 further including the steps of:
    introducing a supplemental compound into the irrigating solution prior to said step of flowing the irrigating solution through the outer housing inlet bore of the cutting accessory; and
    applying the discharge from the cutting accessory window to tissue so that a mixture of irrigating solution and the supplemental compound is applied to the tissue.

11. The method of claim 7 wherein the rate at which irrigating solution is flowed into the outer housing inlet bore and the rate at which said suction is drawn are set so at least 10% of the solution flowed into the outer housing inlet bore is discharged from the outer housing outlet opening onto the surgical site.

12. The method of claim 7, wherein the rate at which irrigating solution is flowed into the outer housing inlet bore and the rate at which said suction is drawn are set so irrigating solution flowed into the outer housing inlet bore is discharged from the outer housing outlet opening onto the surgical site at a rate of at least 2 ml/min.

13. The method of claim 7 wherein:
    the outer housing is formed to have a closed distal end and the outlet opening is proximal to the distal end of the outer housing;
    in said step of actuating the moving shaft, the moving shaft is rotated and the moving shaft is formed to have an outer surface that defines at least one flat that is positioned to selectively come into registration with the outer housing outlet opening in said step of actuating the moving shaft; and
    in said step of flowing an irrigating solution through the outer housing, irrigating solution is flowed over the flat of said moving shaft so that, when the flat comes into registration with the outlet opening of the outer housing, irrigating solution is pulse discharged through the opening.

14. The method of claim 13, wherein in said step of discharging irrigation solution through the outer housing outlet opening, irrigating solution is discharged proximally away from the distal end of the outer housing.

15. The method of claim 7, wherein a maximum of 20% of the irrigating solution flowed into the outer housing inlet bore is discharged from the outer housing outlet opening to the surgical site.

16. A method of performing surgery in a sinus passageway, a nasal passageway or the throat, said method comprising the steps of:
   positioning a cutting accessory in the sinus passageway, the nasal passageway or the throat, the cutting accessory having:
      an elongated outer housing with opposed proximal and distal ends, an inlet bore in the proximal end and an outlet opening in the distal end; and
      an elongated tubular moving shaft within the outer housing, the moving shaft having opposed proximal and distal ends, a tissue working member attached to the distal end and an opening adjacent the distal end;
   applying the cutting accessory to a surgical site to perform the surgical procedure, wherein, in said step, the outer housing distal end and the tissue working member are directed towards tissue at the surgical site;
   actuating the moving shaft to perform a surgical procedure on tissue to which the cutting accessory is directed;
   creating a mixture of a topical medicine and irrigating solution;
   simultaneously with said actuation of the moving shaft, flowing the mixture through the outer housing inlet bore and an interstitial space between the cutting accessory outer housing and the moving shaft to the outer housing;
   discharging the mixture from the outer housing distal end opening so that simultaneously with said actuation of the cutting accessory mixture is discharged onto the tissue at which the surgical procedure is being performed by the cutting accessory; and
   simultaneously with said actuation of the moving shaft, drawing a suction through the moving shaft so that, when the cutting accessory is applied to the surgical site, fluid is drawn through the moving shaft distal end opening.

17. The method of claim 16, wherein said steps of creating the topical medicine-and-irrigating solution mixture and flowing the mixture through the outer housing inlet bore are performed by:
   pumping the irrigating solution from a supply source into the outer housing inlet bore; and
   introducing into the irrigating solution pumped from the supply source the topic medicine to create the mixture after said step of pumping the irrigating solution from the supply source.

18. The method of claim 1 wherein said steps of cleaning the distal end of the endoscope and drawing a suction through the cutting accessory are performed simultaneously.

* * * * *